United States Patent [19]

Polaert et al.

[11] Patent Number: 5,894,620
[45] Date of Patent: Apr. 20, 1999

[54] ELECTRIC TOOTHBRUSH WITH MEANS FOR LOCATING DENTAL PLAQUE

[75] Inventors: Rémy Polaert, Villecresnes; Jean-Pierre Hazan, Sucy-En-Brie; Serge Gourrier, Paris, all of France

[73] Assignee: U.S. Philips Corporation, New York, N.Y.

[21] Appl. No.: 08/793,511

[22] PCT Filed: Jun. 26, 1996

[86] PCT No.: PCT/IB96/00608

§ 371 Date: Feb. 24, 1998

§ 102(e) Date: Feb. 24, 1998

[87] PCT Pub. No.: WO97/01298

PCT Pub. Date: Jan. 16, 1997

[30] Foreign Application Priority Data

Jun. 28, 1995 [FR] France ..................... 95 07785
Dec. 13, 1995 [EP] European Pat. Off. .......... 95402808

[51] Int. Cl.⁶ .................. A61C 3/00; A46B 13/02
[52] U.S. Cl. ................... 15/22.1; 433/29; 433/215
[58] Field of Search ................ 15/22.1, 28, 105, 15/167.1; 433/29, 215; 600/476, 477

[56] References Cited

U.S. PATENT DOCUMENTS

| | | | |
|---|---|---|---|
| 3,261,978 | 7/1966 | Brenman | 15/105 |
| 3,667,454 | 6/1972 | Prince | 15/22.1 |
| 4,479,499 | 10/1984 | Alfano | 433/29 |
| 4,779,173 | 10/1988 | Carr | 15/105 |
| 5,306,143 | 4/1994 | Levy | 433/29 |

FOREIGN PATENT DOCUMENTS 3-251207  11/1991  Japan .......................... 15/105

*Primary Examiner*—Randall E. Chin
*Attorney, Agent, or Firm*—Edward W. Goodman

[57] ABSTRACT

Electric toothbrush comprising means for locating dental plaque An electric toothbrush comprises means (1, 22) for emitting excitation radiation towards teeth (10), means (2, 24) for detecting luminescence return radiation emitted by affected tooth areas, optical fibre means (4a, 4b, 4c) for guiding the excitation radiation, and electrical means (14, 15) for imposing a brushing rhythm. The optical fibre means pick up a narrow beam of return radiation and guide it to the detection means (24) which comprise filter means (40, 42) for extracting at least one useful signal component from a noise component, the useful signal component being in synchronism with the brushing rhythm, the detection means (24) converting the useful signal into a location signal (44) revealing the affected areas.

4 Claims, 3 Drawing Sheets

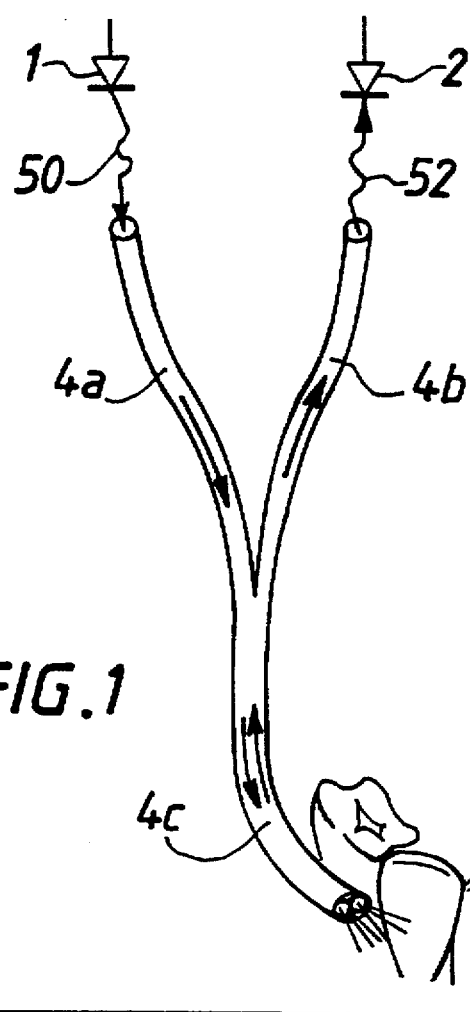
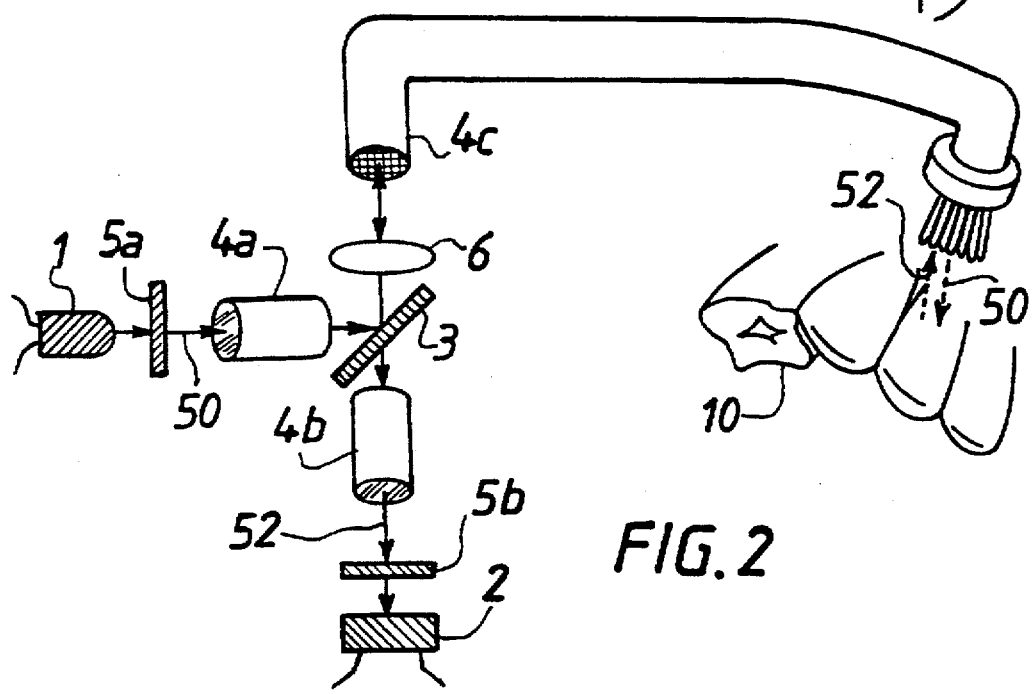
FIG.1
FIG.2

ELECTRIC TOOTHBRUSH WITH MEANS FOR LOCATING DENTAL PLAQUE

BACKGROUND OF THE INVENTION

The invention relates to an electric toothbrush having cleaning bristles for personal care, comprising:

means for emitting excitation radiation towards teeth, means for detecting luminescence return radiation emitted in response to excitation radiation from affected tooth areas, optical fibre means for guiding the excitation radiation to the proximity of the teeth, electrical means for imposing on the toothbrush at least one brushing rhythm.

The presence of dental plaque is the major cause of the development of caries. Plaque is formed slowly and systematically on the tooth surfaces between the routine brushing sessions. When brushing is inadequate or is not effected properly the accumulation of dental plaque, particularly in the interdental spaces, promotes the growth of bacteria which can form acids which attack the protective enamel of the teeth and which give rise to dental caries. It is therefore particularly advantageous when dental plaque can be detected and can be removed in order to prevent its accumulation.

Current practice is generally that the dentist tends to dental care of this kind. Indeed, a third person has the fullest opportunity to examine the teeth and to take action where necessary.

Nevertheless, the document WO 92/06671 is known, which relates to a toothbrush with which self-diagnosis as regards the presence of dental plaque is possible. First of all, a substance capable of fluorescing under the influence of excitation radiation is applied to the teeth. This substance has the property that is absorbed selectively by caries and dental plaque. It can be a fluorescent additive mixed with a toothpaste, so that during cleaning of his teeth the user can detect the presence of dental plaque. For this purpose, the toothbrush comprises a light source which emits the excitation radiation, which is guided to the proximity of the teeth by means of optical fibers. Affected zones of the teeth then emit radiation thus induced, which can be detected visually by the user who examines his teeth either by means of a sensor which actuates visual or audible means, which automatically warn the user when dental plaque is detected. To enable detection it is necessary to first rinse the oral cavity and the toothbrush.

However, such a device has several drawbacks. In particular, the sensor is disposed on the base carrying the bristles, so that it is exposed to direct contact with the toothpaste, the fluorescent additive and saliva. Therefore, such an active sensor should be approved for such a use. Moreover, after it has been used for a certain time the sensor may become opaque, for example as a result of a deposited layer, which reduces its detection capability.

Furthermore, the dimensions of the sensor are not negligible, which makes it necessary to provide an area without bristles which is large enough to ensure that the sensor can receive the induced radiation, which has an adverse effect on the cleaning efficiency.

As a result, the arrangement and the dimensions of the radiation sensor make that it picks up the bulk of the induced radiation emitted by the teeth as a whole. Such a configuration does not allow an accurate detection of the areas affected with dental plaque, which areas are generally situated in the interstices and are therefore not readily accessible because they have limited width dimensions of the order of approximately 1 mm. For an effective cleaning of these areas it is therefore necessary to locate them precisely, i.e. separately and not as a whole.

It is obvious that when the toothpaste with its additive has spread in the oral cavity the described method does not allow the detection of dental plaque. As a matter of fact, the whole oral cavity will emit the induced radiation. It is therefore necessary to rinse the oral cavity so as to ensure that the fluorescent additive only settles on the affected tooth areas.

In order to achieve a correct removal of the dental plaque and to ensure an efficient cleaning, it is therefore necessary to repeat a sequence of operations consisting of brushing the teeth with the toothpaste and its fluorescent additive and subsequently of rinsing the oral cavity as well as the toothbrush itself. This constitutes a tedious sequence of operations to be carried out every day.

SUMMARY OF THE INVENTION

It is an object of the invention to avoid that the user has to perform this tedious sequence of operations, yet allowing the affected areas to be located precisely.

This object is achieved by means of a toothbrush in which the optical fibre means pick up a narrow beam of return radiation and guide it to the detection means which comprise filter means for extracting at least one useful signal component from a noise component, the useful signal component being in synchronism with one of the brushing rhythms, the detection means converting the useful signal into a location signal revealing the affected areas.

Thus, the user can precisely determine the location of the areas where he should raise his cleaning effort.

The optical fibre means can be formed by a single optical fibre or by an arrangement of optical fibers.

Preferably, the arrangement of optical fibers forms a narrow band of optical fibers, the band having a narrow dimension which is substantially collinear with a main brushing direction.

When the fluorescent substance is spread in the oral cavity it is evident that in response thereto the oral cavity as a whole will emit the fluorescence signal. Yet, in accordance with the invention, it is possible to detect each movement of the detection means past the dental plaque, which is usually situated in the interdental areas. In the detector a useful modulated signal is generated in that there are alternately areas with dental plaque and areas without dental plaque. This results in the appearance of a useful luminous signal which, owing to the existence of the brushing rhythm, is converted into a modulated electric signal having a rhythm which is identical to or which is a multiple of the brushing rhythm. With the aid of the filter means, which operate either by synchronous detection or by selective filtering centered on the brushing rhythm, it is possible to free the fluorescence signal from noise generated by the fluorescent substance, which is either spread uniformly in the oral cavity or which is carried along by the movement of the toothbrush, and to obtain a location signal which reveals the presence of dental plaque.

A first type of variant, which does not require the dispersion of the additive over the teeth, consists of the measurement of the remanence of the luminescence induced by the excitation radiation. As a matter of fact, it has been found that dental imperfections have a luminescence whose remanence differs from that of the healthy tooth areas.

A second type of variant consists of the use of a fluorescence substance, for example fluorescein, dispersed in a suitable medium, or a toothpaste or a dental gel containing the fluorescent substance. The return radiation is consequently fluorescence radiation. This mode of operation differs from the preceding mode in that the return radiation lies in a waverange which differs substantially from that of the excitation radiation. In this case the steps consist in measuring the intensity of the return radiation.

The user can be warned by an audible signal and/or by a visible signal, which is triggered when the detection means indicate the presence of an affected area.

To help the user, the detection means may supply a control signal which responds selectively to the electric-motor control in order to change the cleaning of the specified areas, for example by influencing the brushing rhythm.

These and further aspects of the invention will be apparent from and will be elucidated on the basis of embodiments described hereinafter.

BRIEF DESCRIPTION OF THE DRAWINGS

The invention will be more fully understood with the aid of the following Figures, given by way of non-limitative examples and in which:

FIG. 1 is a diagram of the operating principle of the toothbrush in accordance with a first embodiment of the invention, FIG. 2 is a diagram of the operating principle of the toothbrush in accordance with a second embodiment of the invention.

DESCRIPTION OF THE PREFERRED EMBODIMENTS

Figure 3:
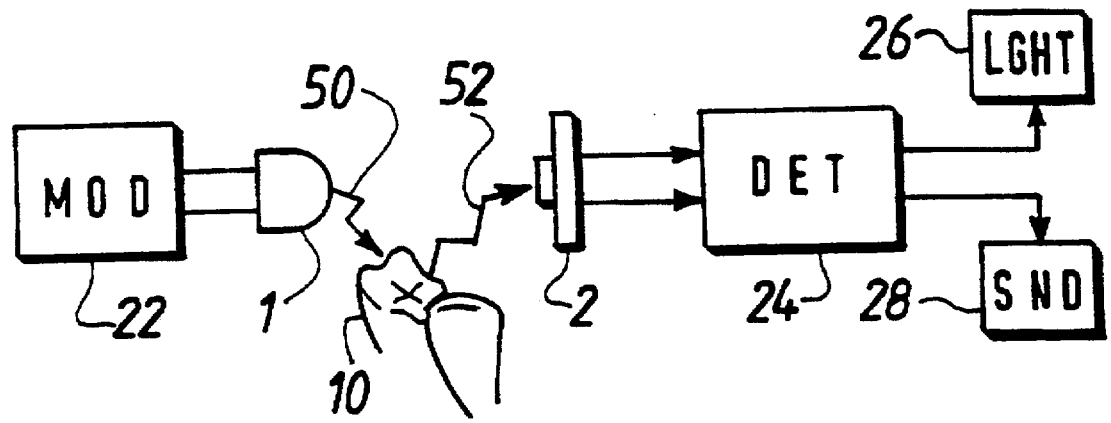
FIG. 3 is a general diagram of the principal electrical means of the toothbrush.

FIG. 1 illustrates the operating principle of the toothbrush in accordance with the first embodiment of the invention. A light emitter 1 emits excitation radiation 50 consisting of blue or violet light having a spectrum situated in the waverange of, for example, approximately 400 to 500 nanometers. This excitation radiation is transmitted to the teeth via an optical fibre guide 4a, 4c. The teeth then emit return radiation 42 in response to the excitation radiation 50.

In the variant of the first type the return radiation is situated substantially in the same waverange as the excitation radiation. In this case a luminescence signal is used for which the duration of the remanence of this return radiation is measured.

In the variant of the second type the return radiation is situated in a waverange which differs substantially from that of the excitation radiation. In this case a fluorescence signal is used for which mainly its intensity is measured, fluorescence being a special case of luminescence. The fluorescent substance applied to the teeth generates the return radiation in another part of the light spectrum, for example in the yellow-green region, which ranges from approximately 500 to 600 nanometers.

For each of these variants the return radiation is guided to the light detection means along a return path by an optical fibre guide 4c, 4b, which light detection means comprise for example a photo-transistor 2. In practice, the optical fibre guide is preferably fork-shaped with a first part for guiding the excitation radiation and a second part for guiding the return radiation.

Preferably, intensity-modulated light is used and for the detection a synchronous detection circuit is used which operates in the rhythm of the modulation in order to eliminate the effects of other excitation light sources.

FIG. 2 illustrates the operating principle of the toothbrush in accordance with the second embodiment of the invention. Like elements bear the same reference symbols as in FIG. 1. The light emitter 1 emits the excitation radiation 50 in the direction of a dichroic mirror 3. This excitation radiation can be filtered by means of a filter 5a, which selects the appropriate waverange. A light guide 4a ensures that the excitation radiation can reach the dichroic mirror. The mirror 3 deviates the excitation radiation towards a light guide 4c, which guides the excitation radiation 50 to the proximity of the teeth 10. The return radiation 52 is recovered by the same optical fibre guide 4c that guides it to the dichroic mirror 3 along a reverse path. Since the return radiation lies in another waverange, it now traverses the dichroic mirror and reaches the photo-transistor 2. The return radiation can be guided by means of a light guide 4b. A suitable filter 5b can be arranged after the dichroic mirror 3. Thus, the very area that has received the excitation radiation can emit the return radiation towards the light detector. The affected tooth areas are then located very accurately.

The second embodiment can also use the variant of the first type or of the second type.

FIG. 3 is a general diagram of the principal electro-optical means of the toothbrush. The optical part described with reference to FIGS. 1 and 2 is now represented diagrammatically as the excitation radiation 50 and the return radiation 52. Modulation means 22 MOD activate the emitter 1 to emit intensity-modulated excitation radiation. The excitation radiation 50 reaches the teeth 10, which emit the return radiation 52, which is detected by the photo-receiver 2, which supplies an electric signal to the detection and demodulation means 24 DET. When the electric signal received exceeds a predetermined threshold, the means 24 actuate a light alarm 26 LGHT or a sound alarm 28 SND to warn the user of the presence of dental plaque. The user can thus direct his brushing action.

Figure 6:
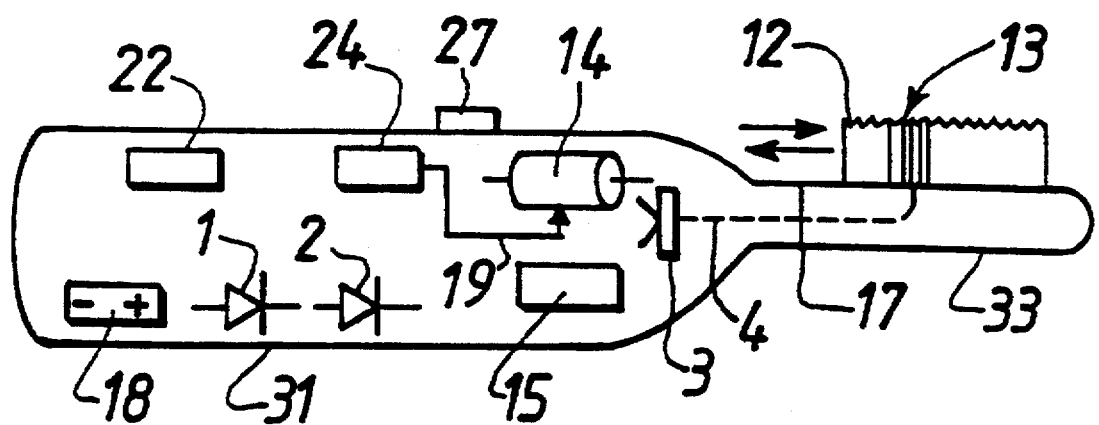
FIG. 6 is a simplified diagram of a toothbrush with electrically controlled brushing.

All the elements which have been described are accommodated in a housing in such a manner that a toothbrush is obtained which can be handled by a user. FIG. 6 shows such an electric toothbrush. It comprises a handle 31 which contains the emitter 1, the receiver 2, the optical fibre guide 4, the modulation means 22, the demodulation and detection means 24 and the dichroic mirror 3 for the second embodiment. Moreover, the electric toothbrush comprises an electric motor 14 which is actuated by a control circuit 15. The handle is extended by a thin part 33 to be introduced into the oral cavity. This thin part comprises cleaning bristles 12 among which the ends 13 of the optical fibers of the guide 4 are implanted. The electric motor 14 imparts to the thin part 33 a reciprocating movement to effect brushing. The operation of the motor 14 can thus be controlled, i.e. accelerated, decelerated and stopped, by means of a control signal 19, in dependence on the signal received by the photo-transistor which is coupled to the ends of the optical fibers included in the brush. The thin part 33 can be removed from the handle 31 at a coupling 17. The electrical power supply is provided by a battery 18. The toothbrush can be turned on and turned off by means of an on/off switch 27.

Figure 4:
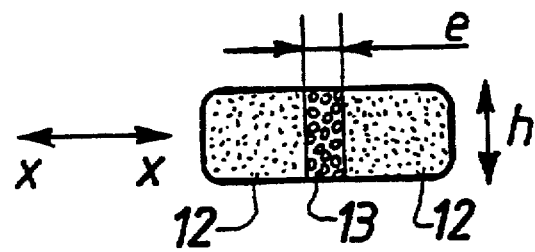
FIG. 4 is a plan view of an example of the arrangement of the optical fibers relative to the cleaning bristles.

The bristles 12 and the ends 13 of the optical fibers can be arranged as shown in FIG. 4. The axis XX indicates the brushing direction of the electric toothbrush during cleaning. Preferably, the ends 13 are arranged so as to form a narrow band having a width e and a length h, the band being disposed in such a manner that the width e extends substantially parallel to the direction of the brushing reciprocation. This has the advantage that each tooth is examined over its entire height in the direction of the length h of the band and the interdental space is examined with enough accuracy for correctly locating affected tooth areas in the direction of the width e of the band. The narrow band defined by the ends 13 is surrounded by the cleaning bristles 12. Alternative arrangements are also possible, the said band being disposed for example at one side of the bristles. The optical fibers have a diameter (250 micrometers) quite close to that of the cleaning bristles (170 micrometers). They can be made of, for example, polymethyl methacrylate. The fibers and the bristles have substantially the same flexibility. By providing for example three rows of 20 optical fibers a detailed examination is obtained, even in the hard-to-get-at interdental areas.

The small diameter of the optical fibers ensures a satisfactory location of dental plaque. As a matter of fact, the relationship between the amplitude of the signal and the distance separating the ends of the optical fibers from the detected zone depends directly on the diameter of the optical fibers used. The detection sensitivity is an inverse function of the distance, the variation of the sensitivity as function of the distance being more pronounced as the diameter of the optical fibers is smaller. Thus, for optical fibers having a diameter of 250 micrometers the detected signal is divided by 2 in the case of a distance of approximately 250 micrometers. These parameters of the proximity and the narrowness of the band of optical fibers help to limit the entrant beam and are important in order to obtain detection means having a high performance.

The detection means 24 measure either the remanence of the luminescence in accordance with the variant of the first type or the fluorescence level in accordance with the variant of the other type.

The fluorescent substance can be applied either by first rinsing the oral cavity with the fluorescent substance or by applying a toothpaste or dental gel containing the fluorescent substance. On the other hand, it may be desired to detect the affected areas either after having removed the surplus of fluorescent substance from the oral cavity, or during brushing while the fluorescent substance is present.

The invention mainly concerns itself with the last-mentioned case, in which the return radiation comprises a substantial d.c. component which disturbs the detection of dental plaque. It can be seen that the signal component caused by the mixture of saliva, toothpaste and fluorescent substance, which moves inside the oral cavity, differs from the signal component caused by the fluorescent substance having settled on the dental plaque. Indeed, since the dental plaque is mainly located along interstitial lines at the junctions between the teeth, the reciprocating movement imposed on the ends of the optical fibers disposed along a line substantially perpendicular to the direction of this movement will result in a modulation of the detected electric signal which is related to the brushing frequency. This brushing movement comprises, for example, a rapid translatory movement at a frequency near, for example, 75 Hz. It may be coupled to a slow alternating oscillatory/rotary movement through ±3° at a rate of 3 cycles per second. With these combined movements the signal detected in the case of dental plaque comprises a first component around 75 Hz having higher harmonic frequencies and a second component around 3 Hz. The last-mentioned component corresponds more in particular to the area of dental plaque adhering to the bases of the teeth close to the gums.

By incorporating in the detection means a filter circuit which is centered on the brushing frequencies used, it is possible to detect the presence of the dental plaque even if the fluorescent substance contained in the toothpaste is either uniformly distributed in the oral cavity or is carried along by the movement of the toothbrush.

Figure 5:
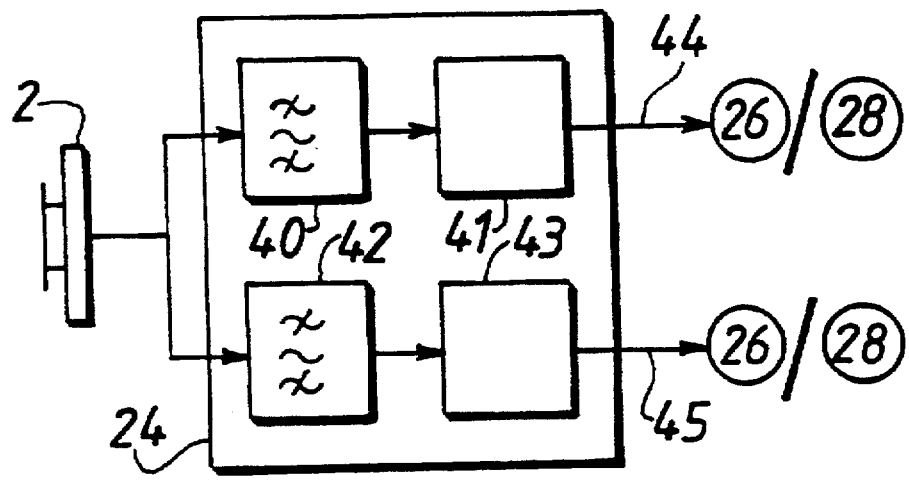
FIG. 5 is an electrical diagram for the separation of the useful signal from the noise signal.

FIG. 5 shows that for detecting the component having the frequency of the translatory movement the detection means comprise a first band-pass filter 40 centered on this frequency, followed by a detection/rectifier stage 41 which supplies the location signal 44 associated with this frequency. Moreover, the detection means may include a second band-pass filter 42 centered on the frequency of the oscillatory/rotary movement, followed by a second detection/rectifier stage 43 which supplies the location signal 45 associated with this second frequency.

Figure 7:
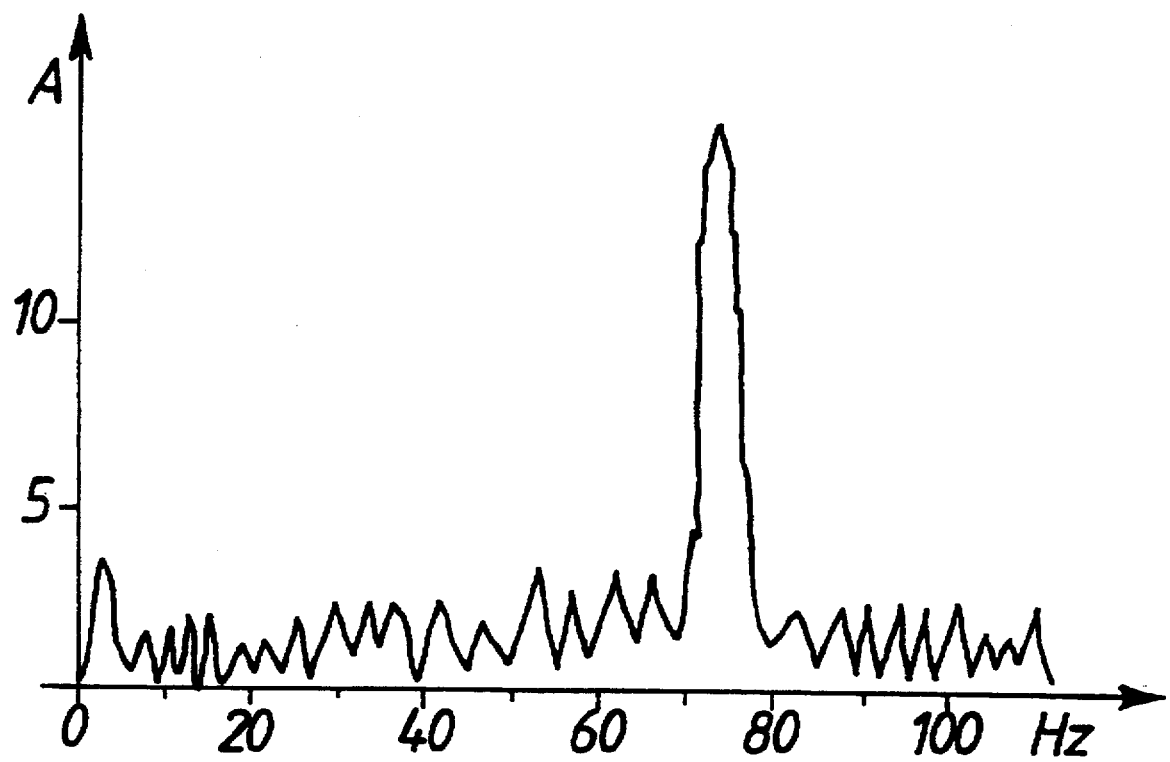
FIG. 7 is a curve indicating a detected useful signal.

FIG. 7 shows a curve representing the amplitude A of the output signal of the photo-transistor 2 as a function of the frequency in Hertz. It is to be noted that the signal has peaks centered on 75 Hz and on 3 Hz mixed with noise. Extracting each of these peaks by filtering provides the location signal or signals which can be used to actuate the means 26, 28 warning the user.

It is evident that such a filtering remains important even when the noise is low, for example when proceeding to the detection of affected areas after having removed any surplus of fluorescent substance spread in the oral cavity.

We claim:

1. An electric toothbrush having cleaning bristles for personal care, comprising:

means for emitting excitation radiation towards teeth, means for detecting luminescence return radiation emitted in response to excitation radiation from affected tooth areas, optical fibre means for guiding the excitation radiation to the proximity of the teeth, electrical means for imposing on the toothbrush at least one brushing rhythm, characterized in that the optical fibre means pick up a narrow beam of return radiation and guide it to the detecting means which comprise filter means for extracting at least one useful signal component from a noise component, the useful signal component being in synchronism with said at least one brushing rhythm the detecting means converting the useful signal into a location signal revealing the affected areas.

2. An electric toothbrush as claimed in claim 1, characterized in that the optical fibre means is formed by one of a single optical fibre and an arrangement of optical fibers.

3. An electric toothbrush as claimed in claim 2, characterized in that the arrangement of optical fibers forms a narrow band of optical fibers, the band having a narrow dimension which is substantially collinear with a main brushing direction.

4. An electric toothbrush as claimed in claim 1, characterized in that the detecting means supply a control signal which selectively modifies said of least one brushing rhythm of specified areas.

* * * * *